(12) United States Patent
Mason

(10) Patent No.: US 6,428,477 B1
(45) Date of Patent: Aug. 6, 2002

(54) DELIVERY OF THERAPUTIC ULTRASOUND BY TWO DIMENSIONAL ULTRASOUND ARRAY

(75) Inventor: Martin K Mason, Andover, MA (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 0 days.

(21) Appl. No.: 09/523,588

(22) Filed: Mar. 10, 2000

(51) Int. Cl.⁷ ................................................ A61B 8/14
(52) U.S. Cl. .................... 600/437; 600/439; 601/2; 601/3; 604/20; 604/458
(58) Field of Search ............... 601/2, 3, 4; 600/437, 600/439, 407; 604/20, 458

(56) References Cited

U.S. PATENT DOCUMENTS

| | | | | |
|---|---|---|---|---|
| 4,893,624 A | * | 1/1990 | Lele | |
| 5,229,933 A | | 7/1993 | Larson, III | 364/413.25 |
| 5,431,167 A | | 7/1995 | Savord | 128/660.07 |
| 5,460,181 A | | 10/1995 | Seyed-Bolorforosh | 128/661.01 |
| 5,485,843 A | | 1/1996 | Greenstein et al. | 128/661.09 |
| 5,558,092 A | * | 9/1996 | Unger et al. | |
| 5,563,346 A | | 10/1996 | Bartelt et al. | 73/626 |
| 5,664,570 A | * | 9/1997 | Bishop | |
| 5,678,552 A | | 10/1997 | Savord | 128/661.01 |
| 5,709,209 A | | 1/1998 | Friemel et al. | 128/660.07 |
| 5,718,227 A | | 2/1998 | Witlin et al. | 128/660.02 |
| 5,725,482 A | * | 3/1998 | Bishop | |
| 5,735,796 A | | 4/1998 | Granz et al. | 600/439 |
| 5,770,222 A | | 6/1998 | Unger et al. | 424/450 |
| 5,793,701 A | | 8/1998 | Wright et al. | 367/7 |
| 5,808,962 A | | 9/1998 | Steinberg et al. | 367/7 |
| 5,823,964 A | | 10/1998 | Liu et al. | 600/454 |
| 5,855,557 A | | 1/1999 | Lazenby | 600/443 |
| 5,860,928 A | | 1/1999 | Wong et al. | 600/453 |
| 5,913,823 A | | 6/1999 | Hedberg et al. | 600/443 |
| 5,928,151 A | | 7/1999 | Hossack et al. | 600/443 |
| 5,947,904 A | | 9/1999 | Hossack et al. | 600/458 |

* cited by examiner

Primary Examiner—Marvin M. Lateef
Assistant Examiner—Jeoyuh Lin
(74) Attorney, Agent, or Firm—John Vodopia

(57) ABSTRACT

A fully steerable two-dimensional ultrasound array delivers a therapy by steering and selective focusing of beams. In some systems, the ultrasound array also includes an imaging functionality to simultaneously perform diagnostic imaging and delivery of a therapy. In one example, the two-dimensional ultrasound array includes a controller that controls beam forming and focusing to scan the focal point of the beam in a pattern within an identified structure of a image. Tissue is thus scanned using a sharply focused beam that is suitable for delivering a therapy such as a hyperthermia therapy or a therapy utilizing delivery of a pharmaceutical via microspheres. Imaging and therapy proceed either simultaneously or separately by operator selection. Simultaneous operation of imaging and therapy delivery are attained using a focused, scanned beam in which a focused beam that delivers intensity levels suitable for heating tissue or for bursting microspheres is pulsed. Reflected signals from the pulses are detected and used to create an image in the manner of conventional ultrasound imaging. Ultrasonic beams are sharply focused to generate intensity levels that are suitable for heating tissues in a hyperthermia application and bursting microspheres in a therapy utilizing microsphere-encased pharmaceuticals. The sharply focused echoes are delivered in pulses and reflections from the pulses are detected and used to create an ultrasound image.

24 Claims, 13 Drawing Sheets

ON AXIS

DELIVERY OF THERAPUTIC ULTRASOUND BY TWO DIMENSIONAL ULTRASOUND ARRAY

BACKGROUND OF THE INVENTION

Ultrasound technology is conventionally used in both therapeutic and diagnostic applications. Diagnostic ultrasound generally relates to the imaging of biological tissue using an ultrasound transducer to transmit ultrasonic waves and receive ultrasonic echoes reflected from the tissue. A transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image. Typically usage of higher frequency, lower energy ultrasonic waves yields better quality images.

Therapeutic ultrasound applications include hyperthermia treatment and ultrasound-assisted administration of bioactive materials. Hyperthermia treatment comprises heating body tissues, such as tumor tissue, with focused ultrasonic waves to reduce the size or retard the growth rate of the tissue. Therapeutic ultrasound heating effects are enhanced by introduction of microbubbles into the treated tissue region.

Ultrasound-assisted administration of bioactive materials typically includes the operations of enclosing a bioactive material in vesicles, applying a quantity of the vesicles systemically to a patient, and monitoring the vesicles to determine when a suitable quantity of the vesicles are located in a region of interest. One technique for monitoring the vesicles is imaging with diagnostic ultrasound. When the vesicles are located in the region of interest, therapeutic ultrasonic waves are applied to the region of interest to rupture the vesicles and release the bioactive material, thereby attaining targeted delivery of the bioactive material or agent directly to the region of interest. Therapeutic ultrasound treatment most suitably involves application of lower frequency ultrasonic waves to attain low attenuation in contrast to the higher frequencies that are advantageous for diagnostic imaging to obtain better resolution.

One example of a combined diagnostic and therapeutic ultrasound application is disclosed in Unger et al in U.S. Pat. No. 5,558,092 in which ultrasonic imaging is performed in a region of a patient while simultaneously applying therapeutic ultrasonic waves to the region to rupture vesicles administered to that region for various purposes, such as the targeted release of a bioactive agent combined with the vesicles.

The ultrasonic transducer assembly disclosed by Unger et al. comprises a plurality of therapeutic transducer elements for generating therapeutic ultrasonic waves, and a plurality of diagnostic transducer elements for generating and/or receiving diagnostic ultrasonic waves arranged on a common platform having a substantially planar upper surface. The therapeutic transducer elements are disposed on the planar surface of the platform central to the diagnostic transducer elements. The diagnostic transducer elements are positioned outward from the centrally located therapeutic transducer elements to enlarge the field of view of the ultrasonic transducer assembly, increase imaging sensitivity and increase the image resolution.

Unger et al. proposes several transducer configurations that allow separate therapeutic ultrasound delivery and imaging. One proposed array has a two dimensional matrix of elements that is operated in a multiplexed manner such that sequential linear sets of elements are activated so that a therapeutic sector is stepped across the skin surface of the patient. The Unger et al. ultrasonic system is thus used for shallow operation near the skin surface. The linear array of therapeutic transducer elements can be operated in a continuous wave mode or in a pulse repetition frequency (PRF) mode as selected by an operator. The amount of energy supplied to the therapeutic transducer elements and the treatment depth can be controlled by the operator.

The multiplexed, two-dimensional array disclosed by Unger et al. insonifies tissue focused at a particular depth both for diagnostic and therapeutic purposes. In one embodiment, an external transducer array contacts the skin to image and deliver therapy to a plane of tissue just below the skin. In another embodiment, an intracavitary probe incorporates a transducer assembly that encircles the probe shaft just below the tip for usage in either endovaginal or endorectal imaging for therapeutic and diagnostic usage focused in a curved plane of tissue enclosing and adjacent to the imaged cavity.

Several problems reduce the utility of conventional systems that combine diagnostic and therapeutic ultrasound application. For example, diagnostic ultrasonic energy is applied near the imaging surface while many therapeutic procedures should apply energy to deep tissue. Also, the ultrasonic energy for therapeutic application is focused at a particular tissue depth with substantial attenuation as the depth increases. A more effective therapy would deliver an essentially uniform energy throughout a range of depths. Furthermore, conventional systems form two-dimensional images of tissue masses that typically have a three-dimensional structure.

What is needed is a combined diagnostic and therapeutic ultrasound system that images and delivers therapy to a volume of tissue.

SUMMARY OF THE INVENTION

A fully steerable two-dimensional ultrasound array performs simultaneous diagnostic imaging and delivery of a therapy by beam forming and steering by selective focusing of beams. In one example, the two-dimensional ultrasound array includes a controller that controls beam forming and focusing to scan the focal point of the beam in a pattern within an identified structure of a image. Tissue is thus scanned using a sharply focused beam that is suitable for delivering a therapy such as hyperthermia therapy or delivery of a pharmaceutical via microspheres. Imaging and therapy proceed either simultaneously or separately by operator selection. In one mode of operation, simultaneous operation of imaging and therapy delivery is attained using a focused, scanned beam in which a focused beam, that delivers intensity levels suitable for heating tissue or for bursting microspheres, is pulsed. Reflected signals from the pulses are detected and used to create an image in the manner of conventional ultrasound imaging.

In an alternative mode of operation, therapy is delivered in a continuous-wave mode to gradually heat tissue, burst microspheres, or otherwise stimulate pharmaceutical action. Ultrasound pulses are interspersed with the continuous-wave signal to interrogate the tissue for image formation.

Alternatively, the controller is capable of controlling beam forming and focusing to defocus the beam to match the cross-sectional size of the tissue-of-interest and directing the resulting broad beam at the tissue-of-interest. The broad beam is defocused to have relatively uniform insonation.

A fully steerable two-dimensional ultrasound array performs simultaneous diagnostic imaging and therapy by exploiting the scanning capability of a two-dimensional array. Ultrasonic beams are sharply focused to generate intensity levels that are suitable for heating tissues in a hyperthermia application and for bursting microspheres in a therapy utilizing microsphere-encased pharmaceuticals. The sharply focused echoes are delivered in pulses and reflections from the pulses are detected and used to create an ultrasound image.

A fully steerable two-dimensional ultrasound array performs imaging and delivery of a therapy by beam forming and steering so that a plurality of elements in the array are active simultaneously. The individual elements in the array are activated and relatively delayed so that a resultant ultrasonic beam is formed and directed in a controlled direction with a focal point set at a desired depth. The ultrasonic beam is controlled to direct the beam in a selected direction within a hemisphere having an origin at the face of the transducer. The phased and steerable two-dimensional array delivers ultrasound energy to a volume within a body.

In one application, a two-dimensional array of ultrasonic transducer elements are individually excitable for both imaging and delivery of ultrasonic energy to a three-dimensional volume of tissue. In some embodiments, the pitch of the elements in the array is preferably no greater than one-half the acoustic wavelength of the interrogation signal to form a clean, focused beam with low side-lobe levels.

The pattern of activated elements and relative timing of the elements are controlled to change the size of the transducer aperture, thereby controlling the depth of focus along an interrogation axis of the interrogation volume. The transducer elements can be activated in various selected patterns to determine the size, shape, and position of the insonated volume. The pattern of activated transducer elements can be translated to move the interrogation axis off-center.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE PREFERRED EMBODIMENT(S)

Figure 1:
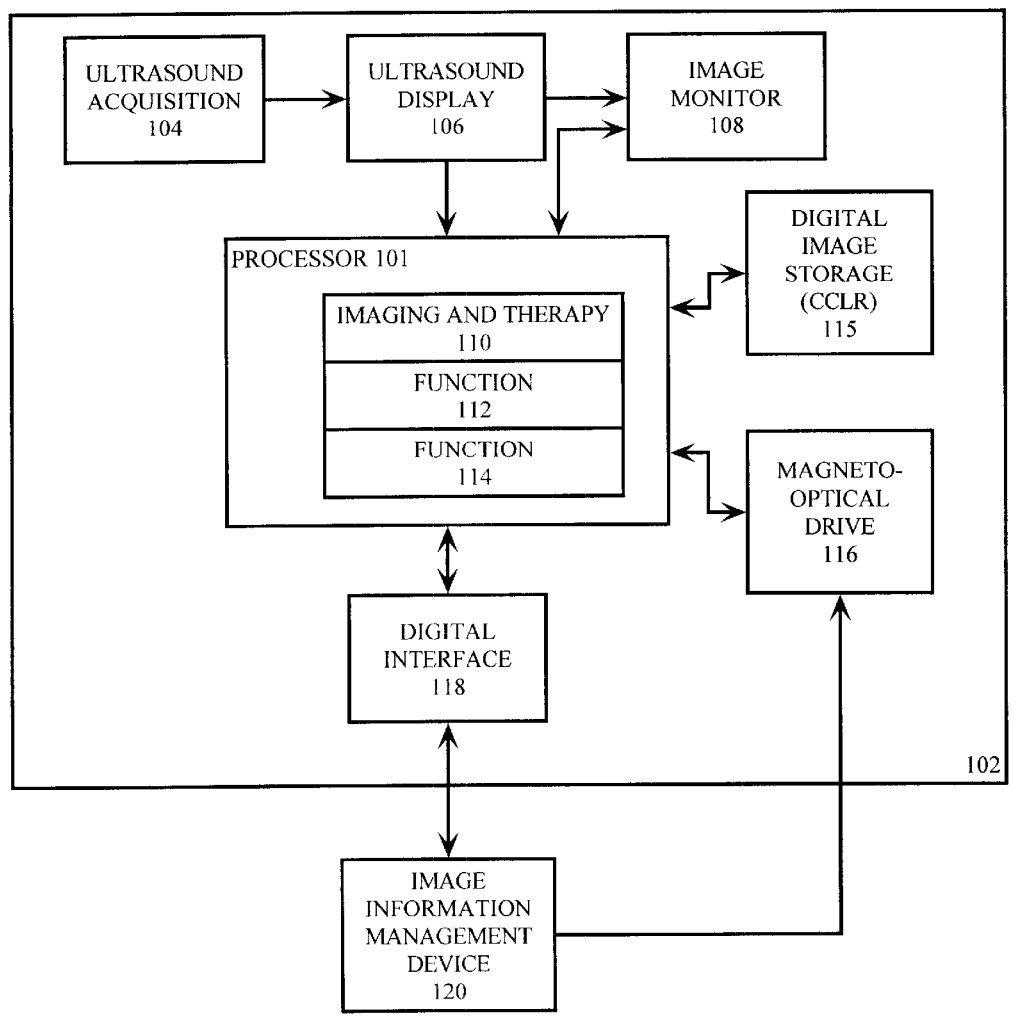
FIG. 1 is a schematic block diagram illustrating an ultrasound imaging system which includes a processes that simultaneously execute diagnostic imaging and delivery of a therapy.

Referring to FIG. 1, a schematic block diagram illustrates an ultrasound device 102 suitable for delivering to biological tissue a therapy such as a hyperthermia therapy or local delivery of a bioactive composition via microspheres. In a first class of applications, the ultrasound device 102 delivers the therapy to a tissue that is localized independently of the ultrasound device 102. For example, various localization techniques such as x-ray imaging, computer-assisted tomography, magnetic resonance imaging, thermography, nuclear scan imaging, fluoroscopy, ultrasound imaging, manual methods such as visual inspection, manual probing and the like, are used to determine the position at which the therapy is delivered. The various localization techniques are applied using a diagnostic device that is external to and independent of the ultrasound device 102.

In a second class of applications, the ultrasound device 102 includes both ultrasound imaging and ultrasound therapy functionality and is capable of simultaneously executing diagnostic imaging and delivering a therapy. Various therapies are possible including hyperthermia therapy, hyperthermia therapy using microspheres to enhance heating, local delivery of a bioactive composition via microspheres, and other suitable therapies. Various hyperthermia therapies function by enhancing uptake of pharmaceuticals in the bloodstream, enhancing the transport rate of thrombolytic substances such as streptokinase, and the like.

The ultrasound device 102 includes an ultrasound acquisition block 104, an ultrasound display block 106, an image monitor 108, a processor 101, a digital image storage 115, a high-density storage such as a magneto-optical disk drive 116, and an integrated digital interface 118.

The ultrasound acquisition block 104 performs conventional ultrasound image acquisition operations including two-dimensional and three-dimensional acoustic imaging, Doppler imaging, and the like. The ultrasound display block 106 performs various ultrasound signal processing and image processing operations, scan conversion, post-processing and the like. The ultrasound display block 106 forms ultrasound images for display and transfers the processed images to the image monitor 108.

The ultrasound acquisition block 104, ultrasound display block 106, and image monitor 108 are controlled by the processor 101 using control operations implemented by programming including a plurality of functions 110-114 that perform various control and analysis operations. One example of a functional package is an imaging and therapy routine 110 that simultaneously executes a diagnostic imaging operation and delivery of therapy. An external image information management device 120 facilitates external storage and viewing of images provided by the US system 102.

Figure 2:
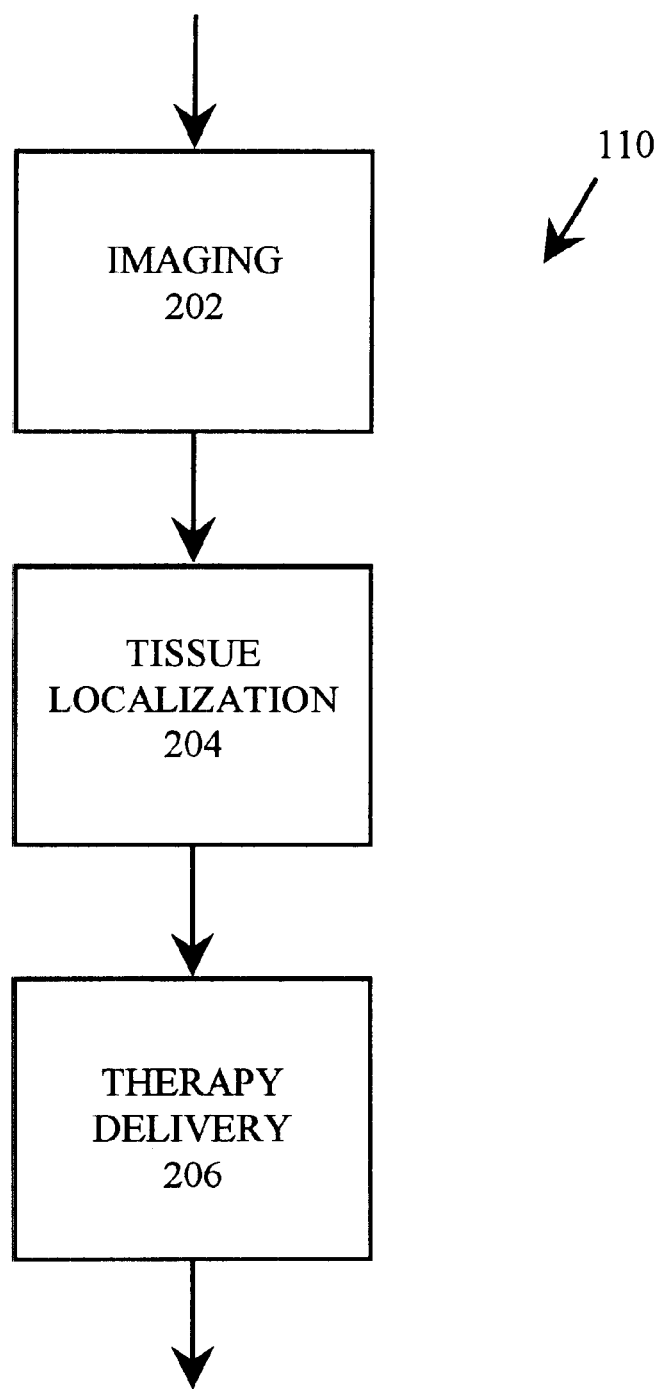
FIG. 2 is a schematic block diagram showing an example of an imaging and therapy routine that simultaneously performs diagnostic imaging and delivery of therapy.

Referring to FIG. 2, a schematic block diagram illustrates an example of an imaging and therapy routine 110 that simultaneously performs diagnostic imaging and delivery of therapy. In an imaging operation 202, the ultrasound device 102 performs ultrasound imaging by scanning a field of view as selected by an operator. The imaging operation 202 continues under control of the operator until the operator determines that the tissue-of-interest for performing therapy is sufficiently contained within the field of view.

The operator then selects a localization functionality which begins a tissue localization operation 204 during which the ultrasound device 102 scans the volume within the field of view to determine the location of the tissue-of-interest within the field. Use of a two-dimensional ultrasound array permits steering of an ultrasound beam to an arbitrary position within the volume. If implemented as a manual operation, the operator identifies borders of the tissue-of-interest, for example via usage of cursors, calipers, line tracing, or similar graphical user interface tools. If implemented as an automatic operation, graphical or image processing functionality is used to automatically determine boundaries of tissue-of-interest. A particular system may include manual functionality alone, or a combination of manual and automatic functionality. The localization operation 204 enables selection of a volume to receive the ultrasonic therapy.

When the boundaries are determined, the ultrasound device 102 enters a therapy delivery operation 206 in which the system is programmed to scan the ultrasonic beam focal point in a pattern within the identified boundaries of the tissue-of-interest to attain uniform insonation. The tissue-of-interest is insonated with a sharply focused beam which generates appropriate intensity levels for delivery of therapy. In one application, the intensity levels generate heat in the tissue-of-interest for hyperthermia therapy. In an alternative application, microspheres containing a therapeutic substance are injected systemically into the body and ultrasonic waves are imposed on the tissue-of-interest to burst the microspheres, releasing the therapeutic substance. The intensity ultrasonic waves that are attained using the sharply focused beam effectively burst the microspheres.

An alternative delivery operation does not use a sharply focused beam but instead defocuses the beam to match the cross-sectional size of the tissue-of-interest and directs the resulting broad beam to the tissue-of-interest. The broad beam is defocused to have relatively uniform insonation.

The ultrasound device 102 utilizes a two-dimensional ultrasound array that effectively images and delivers ultrasonic energy to a volume field, thereby contributing to the combined diagnostic and therapeutic utility of the device. The ultrasound device 102 is highly useful on the basis that the scanning capability of a two-dimensional ultrasound array is exploited to insonate a specific tissue volume and deliver a therapy to the tissue volume. In contrast, conventional ultrasound imaging merely insonifies a plane within the tissue.

The two-dimensional ultrasound array is controlled to insonate tissue volumes having various three-dimensional shapes. For example, the transducer elements can be activated as a pattern of concentric circular rings as viewed from a point of interrogation, and by suitable phasing and range-gating of an interrogation signal to create a substantially spherical interrogation volume. Alternatively, the activation pattern of the transducer elements can be controlled to form concentric ellipses rather than concentric circular rings to generate ellipsoidal interrogation volumes with long axes that can be rotated.

The ultrasound device 102 is suitable for various types of ultrasonic therapy including conventional hyperthermia therapy but also extending to other forms of therapy including various forms of drug, pharmaceutical, biological, genetic therapies and the like. Other therapeutic techniques include usage of ultrasound as a catalyst in assisting chemical reactions such as enzyme and drug interactions. Other techniques include applying ultrasound as an agitator or an ultrasonic cleaner, agitating molecules to improve mixing within the body.

In one example, therapeutic drug delivery systems for site-specific delivery of therapeutics employ microspheres that are filled with a pharmaceutical substance typically in the form of a gas or liquid, but possibly a solid. Typical pharmaceuticals include any type of suitable therapeutic substance including, for example, angiogenic drugs, tumor-toxic drugs, or any other type of substance that is advantageously administered to a local site in the body.

Microspheres are introduced systemically into a patient's body such as by intravenous injection. A therapeutic substance within the microspheres is targeted to specific tissues through the use of ultrasonic energy. The ultrasonic energy is directed to the target area and causes the microspheres to rupture and release the therapeutic substance. The method for diagnostic imaging and therapy delivery extends the imaging and therapy function 110 so as to control the delivery of therapeutic substances to a targeted tissue-of-interest. Microspheres, containing a pharmaceutical substance, are administered to a patient and the microspheres are monitored during the imaging operation 202 to determine whether the microspheres are present within the tissue-of-interest. The operation of delivering the therapy 206 ruptures the microspheres using ultrasound to release the therapeutic substance into the tissue-of-interest.

Figure 3:
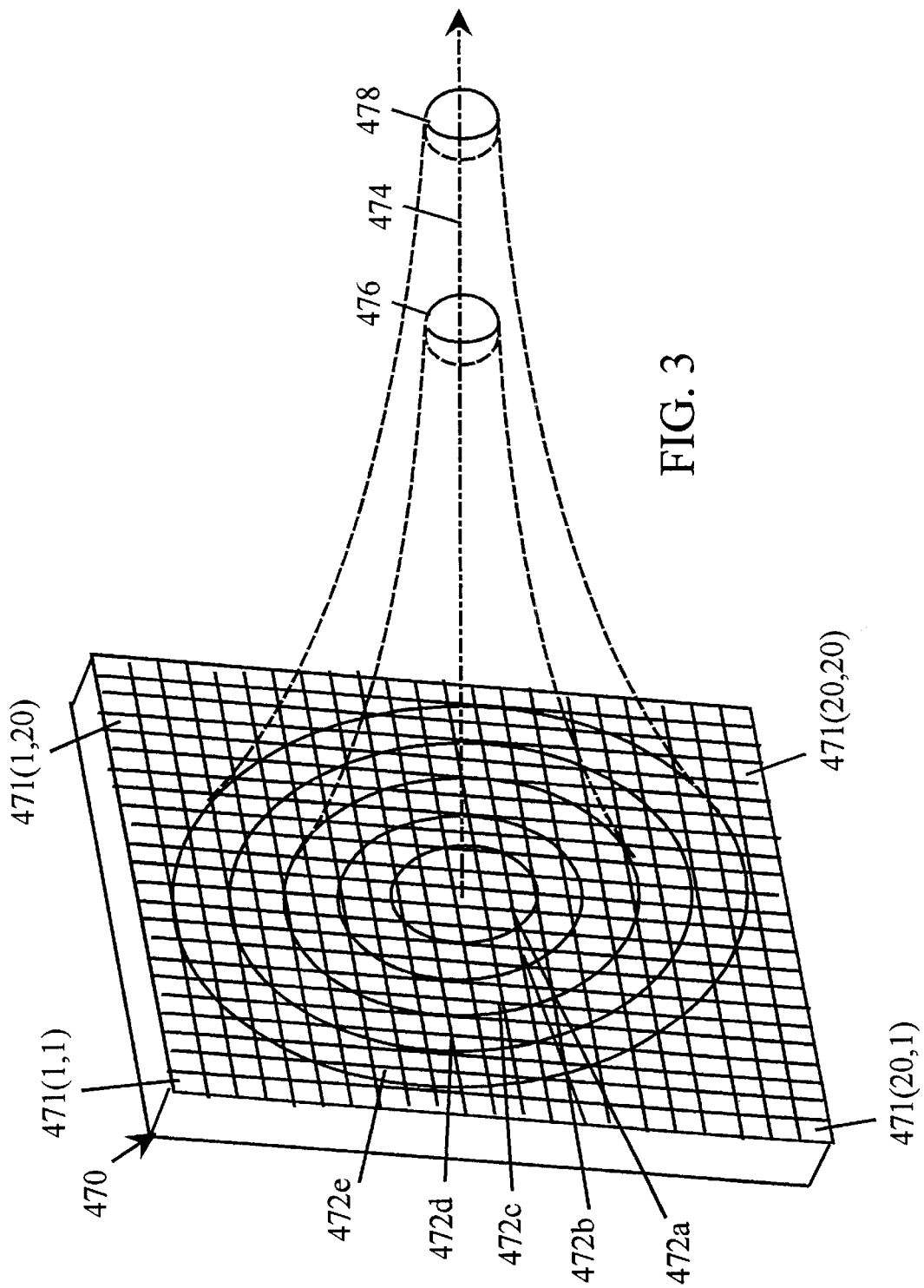
FIG. 3 is a schematic pictorial diagram that illustrates a two-dimensional phased array of ultrasonic transducer elements that can be used to generate the spherical interrogation volume.

Referring to FIG. 3, a schematic pictorial diagram illustrates a two-dimensional phased array 470 of ultrasonic transducer elements 471 that can be used to generate a spherical interrogation volume. The illustrative simplified two-dimensional phased array 470 of ultrasonic transducer elements 471 includes 400 transducer elements arranged in a 20-by-20 matrix. The matrix size is suggested for illustrative purposes only. Any suitable matrix size can be used, based on various considerations including element size, desired imaging resolution, application size, and the like. Corner elements are illustratively labeled as 471(1, 1), 471(1, 20), 471(20, 1), and 471(20, 20). The number of transducer elements used in an application depends on the desired degree of beam-forming and other factors including manufacturing complexity and cost. Individual elements 471 are mutually separated by a suitable technique such as cutting using a dicing saw as is well known to those having ordinary skill in the art.

Concentric rings 472a–e are shown superimposed on the face of the array 470 only for illustrative purposes. Individual transducer elements of the two-dimensional phased array 470 are excited with energy of suitable intensity, duration, and timing so that the array 470 can insonate a three-dimensional volume having a selected shape, size, and position. An array element's excitation is relatively delayed based on the distance of an individual element from the center of the concentric rings 472a–e to approximate the beam forming functionality of a curved surface. For finest beam-forming resolution each element is delayed individually based on the distance from the center of the array. Delays may be set more coarsely so that a group of elements contained within a range of radii from the center of the array are assigned the same delay value. A coarse selection of delays approximates simulation of annular transducer elements.

FIG. 3 depicts a circular form for excitation timing of the array elements. Excitation timing can be imposed to simulate other aperture shapes.

To generate the ring 472a, all transducer elements within the region marked by the ring 472a or having at least a predetermined portion within the ring are excited with suitably delayed excitation signals. Similarly, any other annular region is generated by exciting transducer elements that lie sufficiently within the corresponding annular region on the face of the array 470.

The illustrative two-dimensional phased array 470 performs on-axis focusing of a volume field. Consequently, along the interrogation direction 474, different spherical interrogation volumes, for example 476 and 478, may be created depending on the diameter of the "aperture" created by an outermost ring of transducer elements.

An advantage of the two-dimensional phased array 470 is that the number and diameters of the annular regions can be changed by a simple change in the electrical excitation signals, with no mechanical changes. An additional advantage of the two-dimensional array 470 is the capability not only to change the focal distance of the array but also to change the interrogation direction 474 and modulate the eccentricity of the interrogation volumes. Depending on the physical properties of the transducer elements in the array 470, known analytical and numerical techniques, simulation, and experimentation can be used to determine excitation signals for the transducer elements. The excitation signals constructively interfere to create and rotate interrogation regions including ellipsoidal interrogation regions and regions with other shapes. The illustrative two-dimensional phased array 470 generates, moves, and changes interrogation volumes using electronic control alone.

Figure 4:
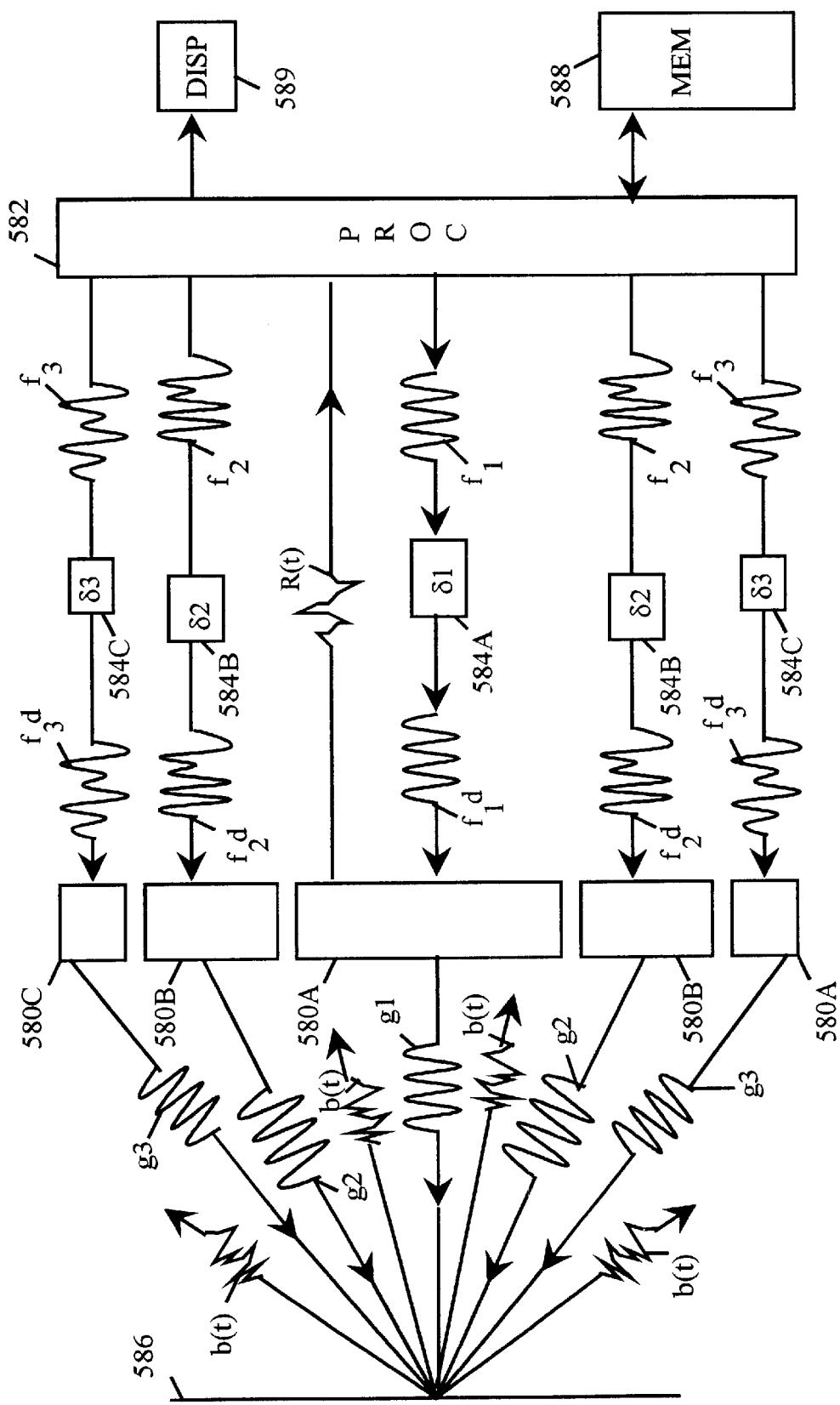
FIG. 4 is a simplified schematic block diagram that illustrates a system for generating interrogation volumes by varying the activation pattern of the transducer elements in the two-dimensional array and the timing/phase relationships of respective transmit and receive signals for different groups of active transducer elements.

Referring to FIG. 4, a simplified schematic block diagram illustrates components and signals of a system for generating interrogation and treatment volumes by varying the activation pattern of the transducer elements in the two-dimensional array and the timing/phase relationships of respective transmit and receive signals for different groups of active transducer elements. The illustrative system generates interrogation and treatment volumes of controlled sizes and geometric shapes including spherical interrogation volumes and ellipsoidal interrogation volumes.

The system may have other configurations but is shown as a two-dimensional phased array that is controlled to simulate a three-ring annular array to facilitate explanation of system operation. The illustrative system includes an array with three active regions 580A, 580B, and 580C, each of which represents a group of transducer elements in the two-dimensional array. The individual elements of the active regions 580A, 580B, and 580C are activated with essentially the same transmit signal and receive signals that are processed substantially in the manner of a single transducer element. Although an emulation of a simple three-ring array is illustrated, the structure of the system also applies to a more general cases of n-ring annular or n-elliptical transducer array emulation.

Conventional processing circuitry 582 generates electrical excitation signals $f_1$, $f_2$, $f_3$ in a sequence of pulses that drive piezoelectric elements of the transducer array. In a simplest single-frequency or "monochromatic" case, the individual excitation signals have the form $f_i(t)=E_i(t)\cos(\omega t)$. Excitation signals $f_1$, $f_2$, $f_3$ are time-delayed by amounts $\delta_1$, $\delta_2$, and $\delta_3$, respectively, either in separate conventional delay circuits 584A, 584B, 584C or by the processing circuitry 582 generating excitation signals $f_1$, $f_2$, and $f_3$. The piezoelectric transducer element groups 580A, 580B, 580C are excited by the respective delayed excitation signals $f_1d$, $f_2d$, $f_3d$. For single-frequency excitation signals the delayed excitation signals have the general form:

$$f_i d = E_i(t)\cos[\omega(t-\delta_i)].$$

A single-frequency excitation signal is depicted for simplification of explanation only, and multiple-frequency excitation signals such as is shown in FIG. 4 for excitation signals $f_2$ and $f_3$ are highly suitable. Excitation signals may contain other frequency components so that the general form of the delayed excitation signals is:

$$f_i d\ i = (W_i, t, \delta_i),$$

where $W_i$ is a set of frequencies included in the spectrum of the respective excitation signal.

Time delay is illustratively shown to define focusing conditions, although those having ordinary skill in the art also know that phase mixing is a suitable technique.

The transducer elements are excited by respective input signals $f_i d$ and emit corresponding ultrasonic output signals $g_1$, $g_2$, and $g_3$ that form the interrogation signal and mutually interfere to focus the interrogation volume at a focal plane 586. Moving particles within the interrogation volume backscatter the ultrasonic signal as a return signal $b(t)$. The back-scattered ultrasonic return signal is converted by one or more of the piezoelectric transducer element groups 580A, 580B, 580C into the electrical return signal $R(t)$, a composite of the electrical return signals generated by each of the transducer elements in the array. After conventional range gating and other suitable signal processing operations such as envelope detection, flow speed and direction are calculated in processing circuitry 582. In a multi-element transducer, conventional beam-forming techniques combine the individual RF signals at individual elements into the composite RF signal $R(t)$ for range-gating and envelope detection.

Processing circuitry 582 typically contains or is connected to conventional signal generation and conditioning circuitry to generate excitation signals $f_1$, $f_2$, $f_3$ as a sequence of pulses that are repeated at a predetermined rate. Similarly, the processing circuitry 582 may contain or be connected to conventional receiving and conditioning circuitry that executes functions such as pre-amplification, sampling, and analog-to-digital conversion. Processing transforms the return signals, either individually or as a composite R(t), from the transducer elements into numerical values suitable for use in diagnostic imaging. Processing circuitry 582 or additional receiver circuitry may also be included to execute spherically symmetrical round-trip beam-forming in the interrogation volume.

A memory circuit 588 is either connected or contained within the processing circuitry 582. The memory circuit 588 accumulates successive values of the return signal R(t) that are used in the calculations of flow speed and direction. The memory circuit 588 may also be used, for example, to digitally store signal profiles used by processing circuitry 582 to generate excitation signals $f_1$, $f_2$, $f_3$. Diagnostic images are available for display to the user on any conventional alphanumerical, graphical or other display device 589 that is driven by an output of the processing circuitry 582. The output results may also be passed on to additional processing, evaluation, or application circuitry.

The transducer generates a spherical interrogation volume to identify boundaries or borders of a tissue mass, for example a tumor, which may be treated using therapeutic insonification of the mass. The ultrasonic transducer output signals $g_1$, $g_2$, $g_3$ have signal forms that constructively interfere to create the spherical interrogation volume.

Excitation signals to the transducer elements in the two-dimensional array may alternatively have signal waveforms that cause constructive interference of the ultrasonic output signals to create ellipsoidal interrogation volumes. To image a spherical interrogation volume, the ultrasonic transducer elements are controlled to generate an envelope E(t) of the output signals so that the range dimension is set equal to the azimuth and elevation dimensions of the interrogation volume. Thus a suitable transducer for generating a spherical interrogation volume is sufficiently fast or broadband that the output signal envelope E(t) is substantially the same as the excitation signal envelope. In practice, the output signal envelope from the transducer element is not exactly the same as the envelope of the excitation signal that forms the electrical input to the piezoelectric transducer element.

The "slower" a transducer element, the greater the difference between the output signal envelope E(t) and the excitation signal envelope, particularly for input excitation signals that have more than one component frequency. Characteristics of the output signal depend on the impulse response characteristics of the corresponding transducer.

Characteristics of the output signal that are used to generate the spherical or elliptical interrogation volumes may be calculated to determine suitable excitation signals either theoretically by deconvolution, simulation, or experimentation. Deconvolution is possible assuming the impulse response function of each transducer is known or capable of estimation. Parameters to generate the corresponding signals may be stored in the memory circuit 588 for use by the processing circuitry 582 in generating the excitation signals $f_1$, $f_2$, $f_3$, not only for a given spherical interrogation volume, but also for the position in space of the spherical interrogation volume, or the position, orientation, and eccentricity of elliptical interrogation volumes.

Figure 8:
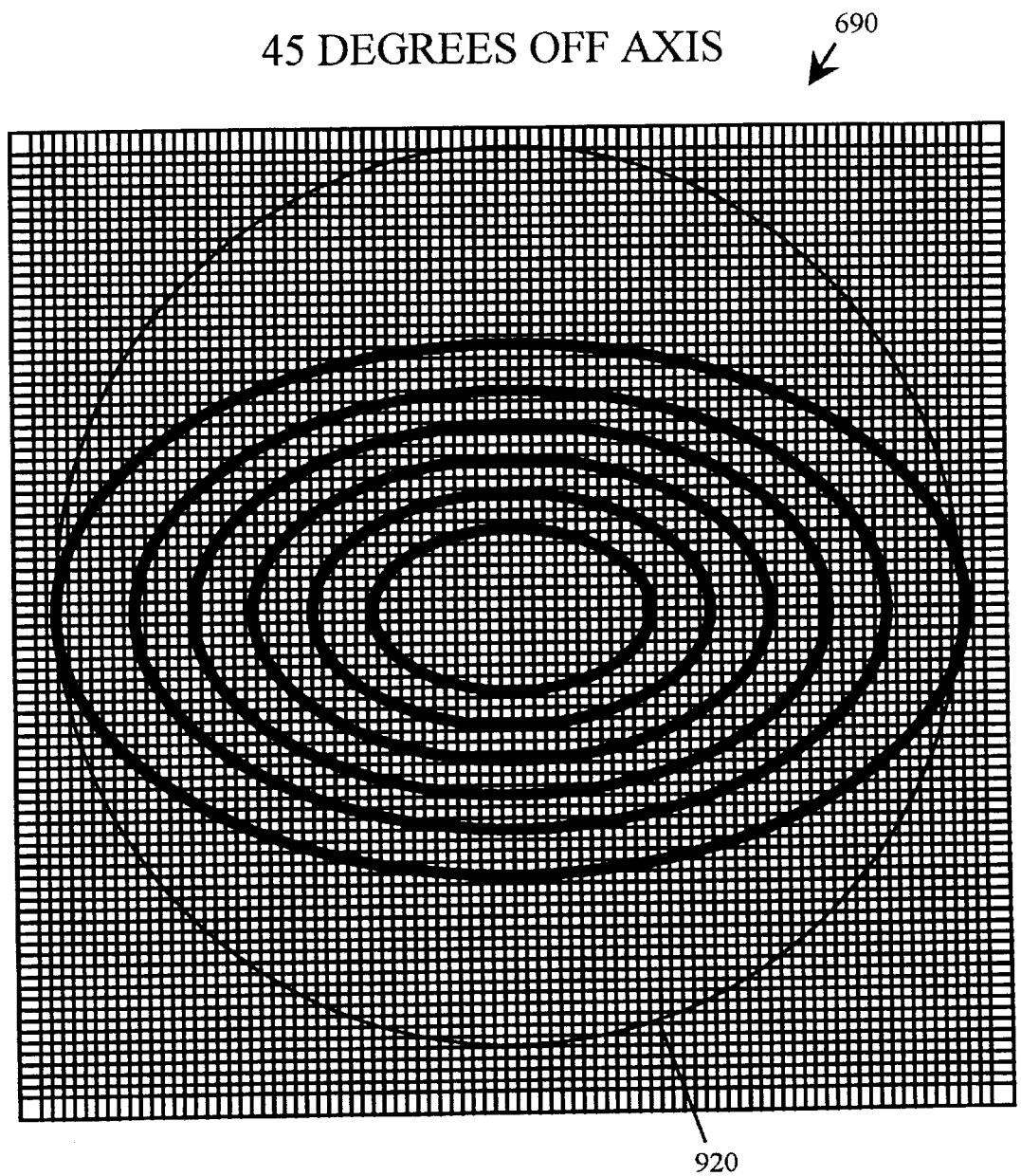
FIG. 8 is a schematic pictorial illustration of an activation pattern configured for a 45° off-axis, centered steering of the two-dimensional array.

Although a perfectly spherical interrogation volume is difficult to attain, a sufficiently spherical interrogation volume is achievable for most applications and generated by creating a wave envelope with a Gaussian range profile of appropriate width. In particular, a suitable array such as the structurally annular array shown in FIG. 3 or an "emulated" annular array as shown in FIGS. 4 and 8 is configured as a pattern of concentric circular transducer elements for the case of on-axis focusing. Functional array elements are activated by appropriate timing and phasing to generate an interrogation volume that is approximately cylindrical. The range dimension of the cylinder is adjusted to equal the lateral dimensions and the "edges" of the cylinder are then "rounded," for example, by using a Gaussian range profile.

The transducer element groups 580A, 580B, 580C correspond to the elements in one of the concentric apertures in a simple three-aperture configuration. Transmit and receive signals are similarly be applied and collected from each of the n element groups in the more general n-aperture case. The return signal R(t) then represents the composite signal from all active elements in the array.

Figure 5:
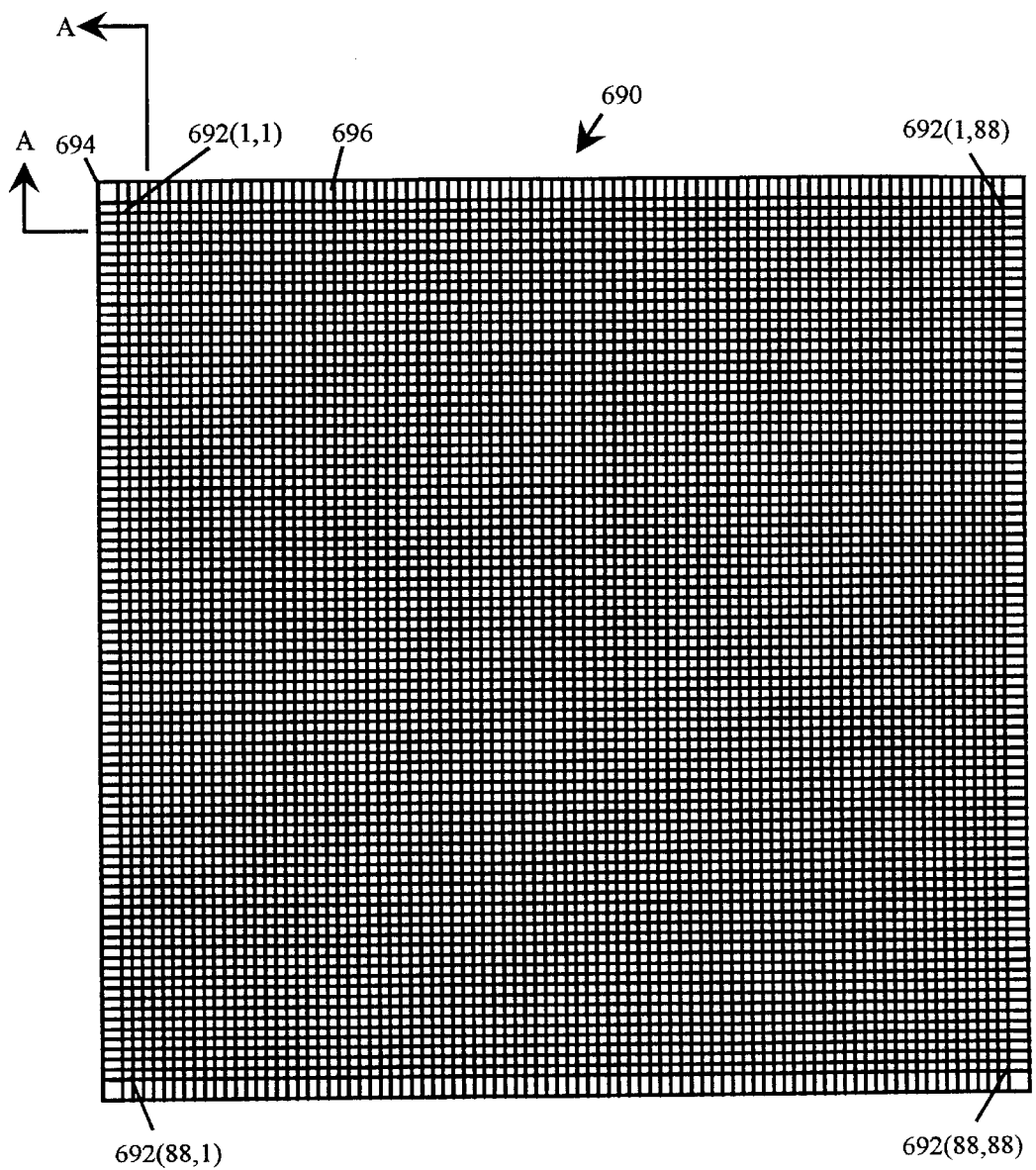
FIG. 5 is a diagram that illustrates a layout of a suitable two-dimensional array with 7744 functional transducer elements.

Referring to FIG. 5, a diagram illustrates a layout of a suitable two-dimensional array 690 with 7744 functional transducer elements that is suitable for generating both spherical interrogation volumes and ellipsoidal interrogation volumes. In the illustrative array 690, 7744 functional transducer elements are arranged in a 88×88 array. The functional elements are activated by electronic transmit signals and receive back-scattered return signals from the interrogation volume. Corner functional elements in the array 690 are labeled 692(1, 1), 692(1, 88), 692(88, 1), and 692(88, 88).

The number of elements in the array 690 need not be 7744 but may be varied depending on considerations such as size, resolution, cost, and manufacturing complexity. Although a square array supports the greatest available range of circular apertures, other array configurations are suitable. Other suitable configurations include, but are not limited to, nxm rectangular configurations, various shapes of polygons, arrays with curved boundaries, and the like.

Illustratively, the array 690 operates at a center frequency in the range of 1.0 to 50.0 MHz and has a pitch P (element spacing) such that P<$\Lambda$/2, where $\Lambda$ is the acoustic wavelength in the medium of propagation. The pitch restriction designates that the transducer elements 692 in the array 690 are no larger than half the acoustic wavelength, so that the inner 88×88 active area of the array 690 is 25$\Lambda$×25$\Lambda$ in size. The specified spatial sampling is sufficient both to produce a suitable approximation to a spherical or elliptical array aperture and also to avoid formation of grating lobes in the beam profile of the phased array.

Figure 6:
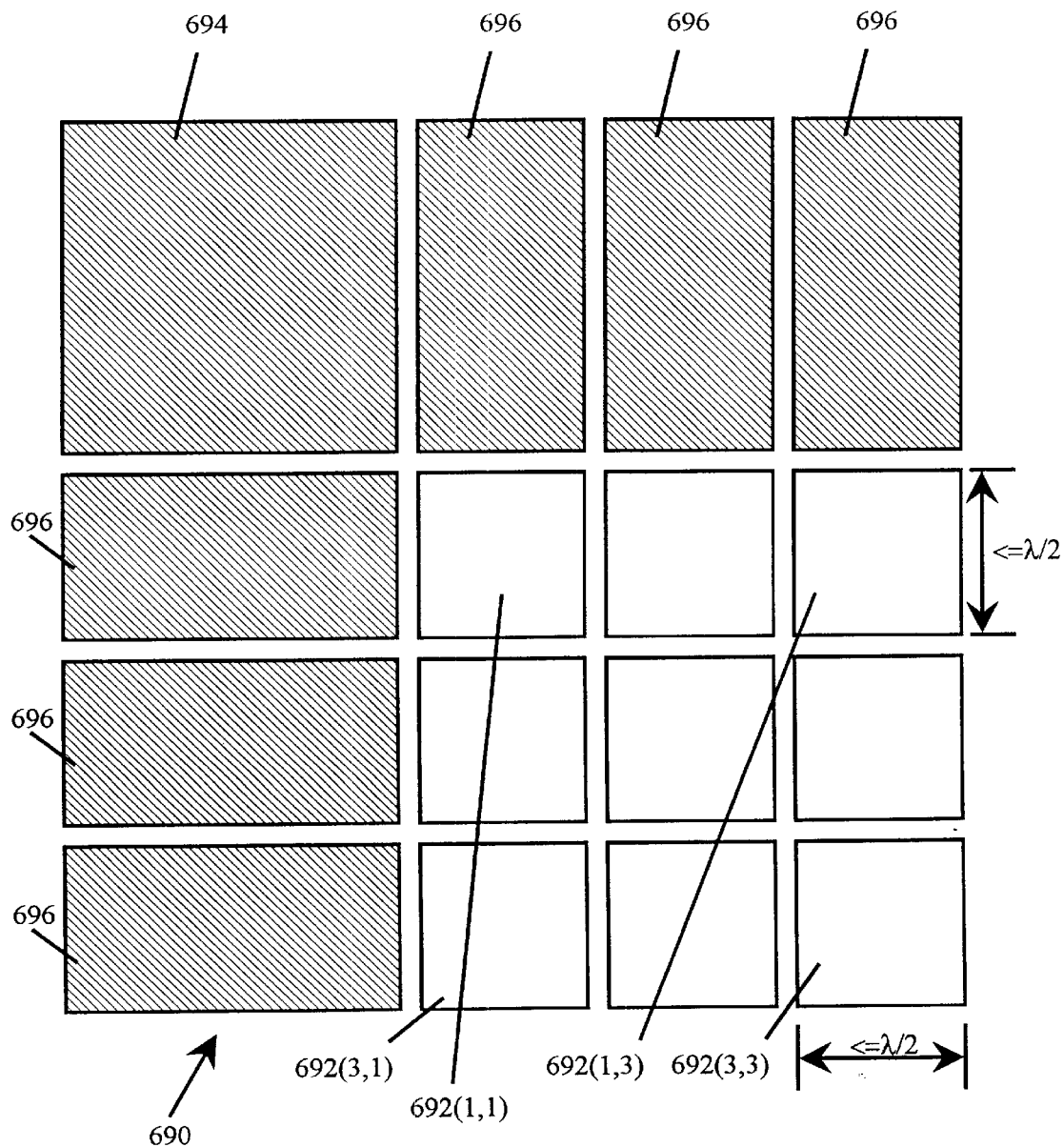
FIG. 6 is a schematic diagram showing both active and inactive transducer elements in a portion (section A—A) of the array depicted in FIG. 5.

Referring to FIG. 6, a schematic diagram shows both active and inactive transducer elements in a portion (section A—A) of the upper left corner of the array depicted in FIG. 5. Non-functional guard elements such as corner element 694 and edge elements 696 are shown shaded, and nine functional elements 692(1, 1), ..., 692(1, 3), ..., 692(3, 1), ..., 692(3, 3) are shown without shading. The guard "edge" of the array including the corner elements 694 and edge elements 696 is illustratively at least twice as wide as the size of a functional element 692 to supply sufficient structural protection for functional elements. The illustrative two-dimensional array includes not only a piezoelectric resonator layer but also a front matching layer to facilitate forward power transfer and a backing layer to attenuate the rearward acoustic signal.

Figure 7:
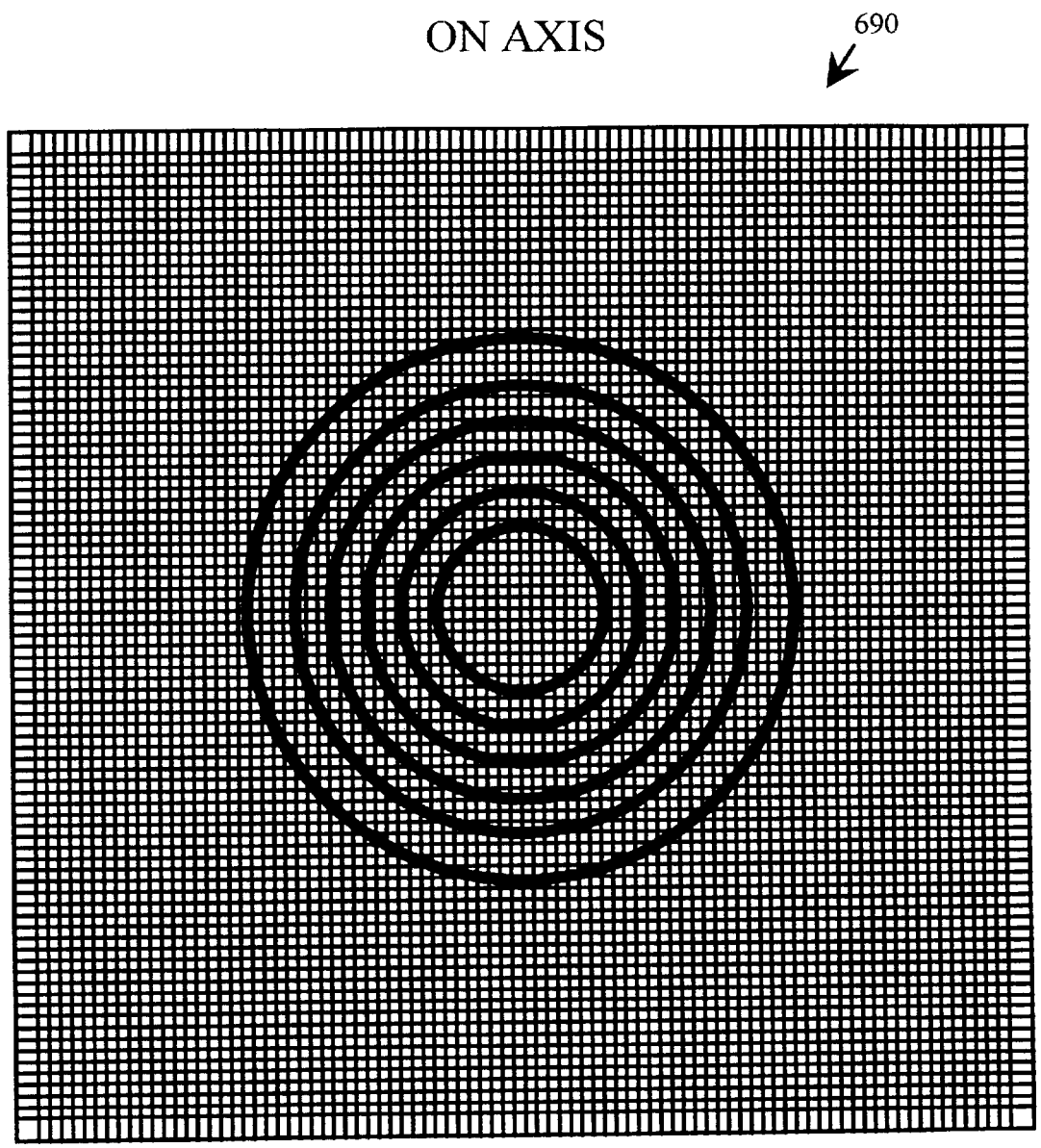
FIG. 7 is a schematic pictorial depiction of an on-axis element activation pattern of concentric circles for generating a spherical interrogation volume.

To produce a spherical interrogation volume, the effective aperture of the two-dimensional array 690 is circular as viewed from the point of interrogation. Thus, when the interrogation beam is focused on-axis, the aperture is circular. When the beam is steered off-axis, the aperture is to be elliptical. FIG. 7 is a schematic pictorial depiction of an on-axis element activation pattern of concentric circles for generating a spherical interrogation volume, and illustrates, for simplicity alone, a set of 12 concentric circular apertures, alternately shaded and non-shaded for clarity, steered on-axis. At near ranges smaller apertures are used since fewer outer "rings" are activated. As range increases the aperture expands by activating more element regions or patterns with larger diameter. Timing delays may be selected with varying coarseness to approximate the beam-forming characteristics of a curved surface or an annular array with array elements of a selected width. Boundaries of aperture contours are determined by the condition that each contour should span a constant phase shift.

Referring to FIG. 8, a schematic pictorial illustration shows an equivalent activation pattern configured for a 45° off-axis in the azimuthal plane, centered steering of the two-dimensional array 690. An ellipse shows a circular aperture as view from 45° A circle 920 represents a set of long axes for scanning in arbitrary planes. The degree of eccentricity that the elliptical element activation patterns have to project as a circle onto a given interrogation focal plane may be determined using known methods such as well known equations for conic sections.

The illustrative two-dimensional array is also capable of adjusting an offset to the center of the set of concentric apertures to control the direction of interrogation. The offset is adjusted by dynamically shifting or translating the center of the concentric apertures; facilitating scanning through the "keyhole" formed by the ribs in a transthoracic scan. Dynamic control of a spherical interrogation volume is not possible using conventional annular or one-dimensional arrays.

Figure 9:
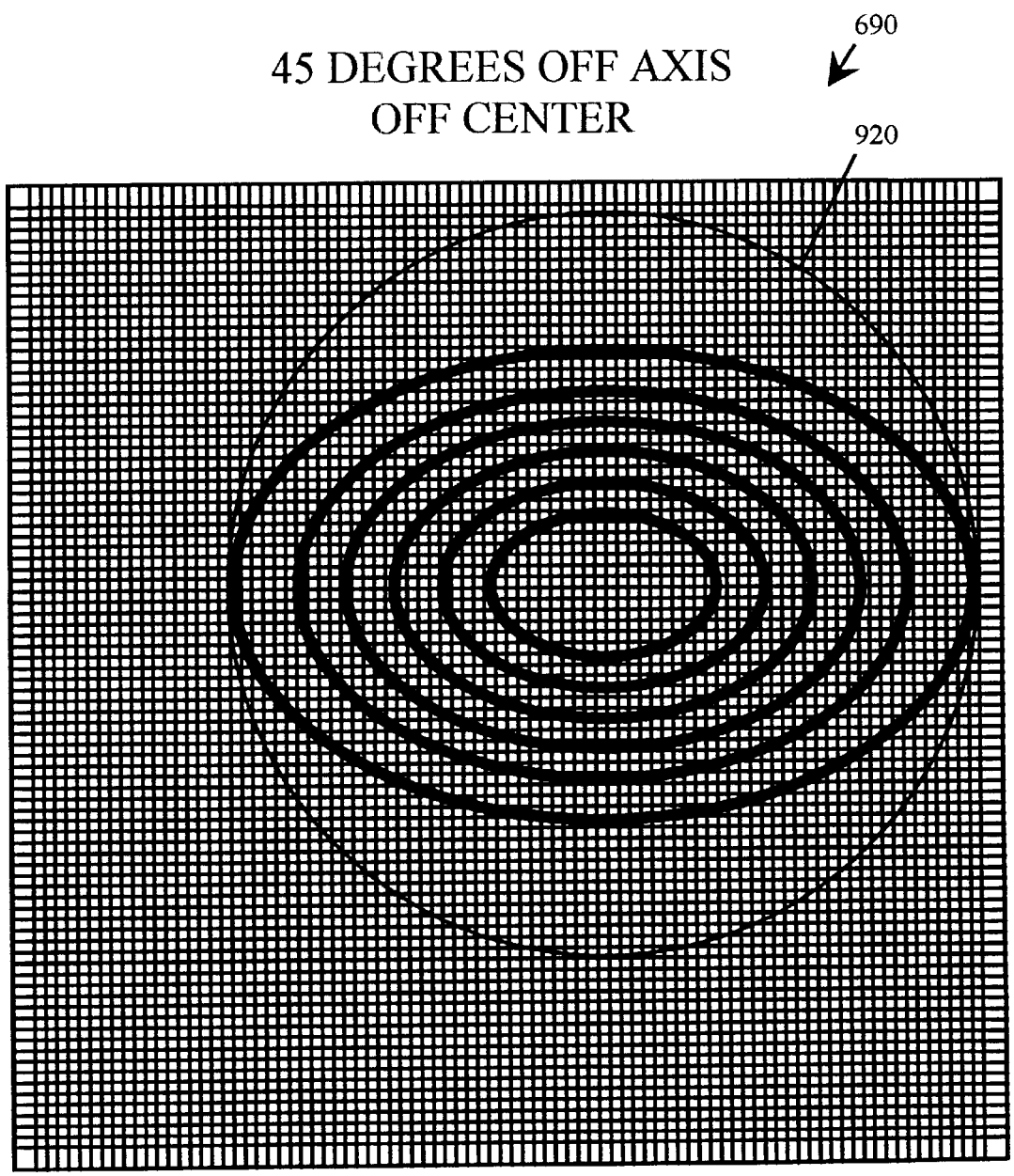
FIG. 9 is a schematic pictorial diagram showing an activation pattern configured for 45° off-axis, off-center steering of the two-dimensional array.

Referring to FIG. 9, a schematic pictorial diagram shows an activation pattern configured for a 45° off-axis scan with an off-center displacement in both the x- and y-directions, and steering of the two-dimensional array. The center of the elliptical activation regions is moved both upward and to the right relative to the center of the array shown in FIG. 8. FIG. 9 also illustrates that the number and size of concentric apertures are adjustable, depicting an activation pattern with eight apertures instead of twelve.

The apertures shown in FIGS. 8 and 9 are selected for illustrative purposes alone. In practice, the two-dimensional phased array can have more or fewer apertures depending on the specific measurement specifications. One advantage of the configuration is that the aperture can be changed without mechanical change. Instead the apertures is changed by activating more, fewer, or different transducer elements, thus by electronically applying appropriate transmit and receive signals to the elements using the same mechanical and electrical structure.

Figure 10:
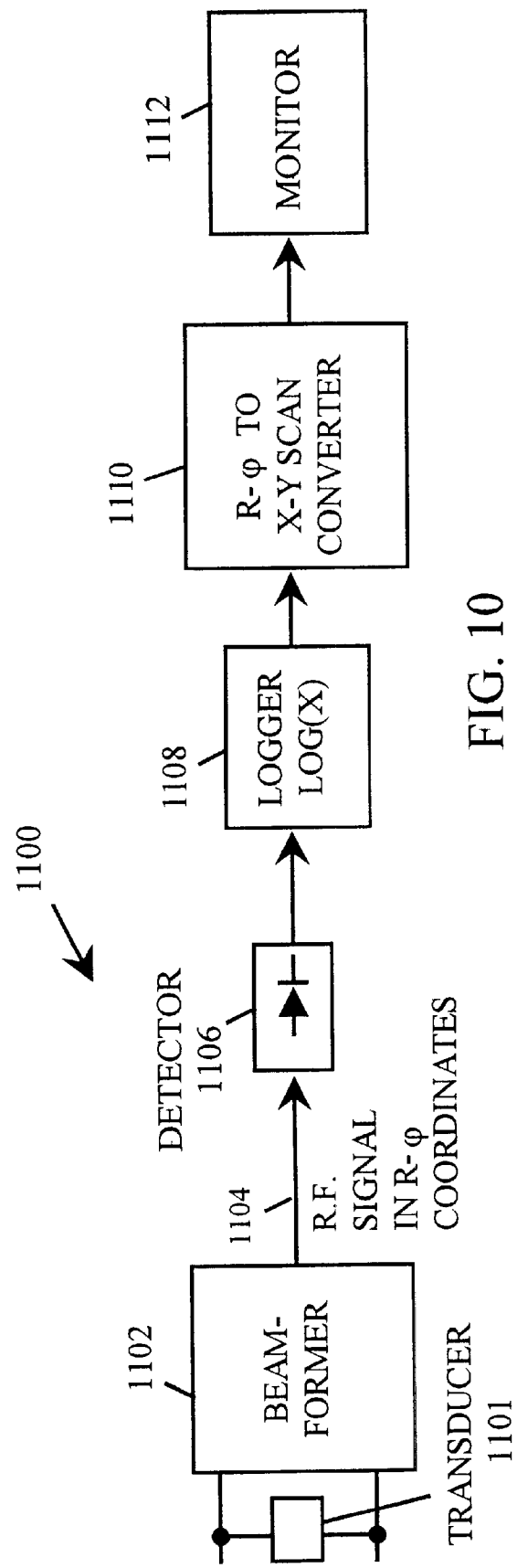
FIG. 10 is a simplified electrical schematic block diagram showing a phased-array acoustic imaging circuit that is suitable for usage in a combined diagnostic and therapeutic ultrasound system.

Referring to FIG. 10, a simplified electrical schematic block diagram shows a phased-array acoustic imaging system 1100 that is suitable for usage in a combined diagnostic and therapeutic ultrasound system. An array of transducers 1101 (only a single transducer is shown for simplicity of description alone) is connected to an input terminal of a beamformer circuit 1102. The same array of transducers is used to both generate a transmit beam and receive reflected pressure pulses. Although transducer 1101 is schematically shown connected directly to beamformer 1102 for clarity, transmit drivers and receive amplifiers are connected between the transducers and the beamformer in a manner well known to those having ordinary skill in the art.

The beamformer circuit 1102 contains a plurality of delay lines for selectively delaying transducer signals and a summing network that combines delayed signals to produce an output electrical signal on line 1104. A beamformer output signal on lead 1104, which typically corresponds to valuation in R-θ coordinates, is processed to generate the final X-Y signals for display on monitor 1112. The output signal on lead 1104 is detected and compressed prior to transmission to a scan converter 1110 which converts the R-θ coordinates to X-Y coordinates. Scan conversion is interposed in the signal path between the beamformer 1102 and the monitor 1112 because beamformer output signals have a large dynamic range and a typical monitor only displays signals with a very limited dynamic range. Accordingly, the beamformer output signal on lead 1104 is applied to a detector circuit 1106.

Detector circuit 1106 is typically an "absolute value" or "square-law" type detector which is schematically illustrated as a diode although other devices may be substituted, as is well known to those having ordinary skill in the art. The detector 1106 is illustratively an absolute value detector. The output signal from detector 1106 contains a DC level related to the magnitude of the input signal and is conveyed to amplifier 1108. Amplifier 1108 reduces the dynamic range of the signal generated by detector 1104 to a signal range suitable for monitor 1112. A typical device is a logarithmic amplifier which generates the output log(x) in response to an input signal x. In other circuits, other data compression devices are known and suitable for substitution for the logarithmic amplifier. Suitable devices include any type of amplifier with a nonlinear transfer characteristic.

Figure 11:
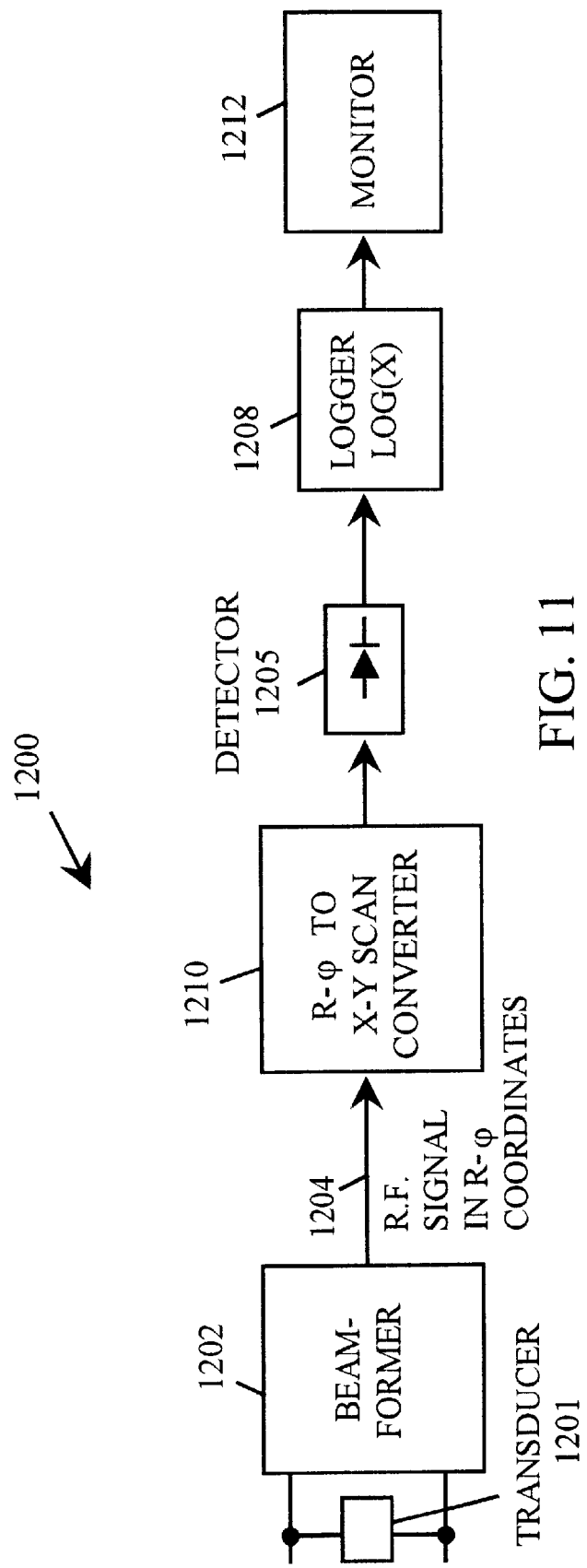
FIG. 11 is a simplified electrical schematic block diagram of an acoustic imaging circuit in which scan conversion is performed prior to signal detection and logging to increase the image resolution.

Referring to FIG. 11, a simplified electrical schematic block diagram shows an acoustic imaging system 1200 in which scan conversion is performed prior to signal detection and logging to increase the image resolution. Resolution of an acoustic image generated by the imaging system 1100 is significantly increased by changing the signal processing order. Specifically, by performing scan conversion before detection and compression, resolution of the image is enhanced without increasing the number of scan lines. In the acoustic imaging system 1200, transducer 1201 and beamformer 1202 correspond to elements 1101 and 1102, respectively, shown in FIG. 10. The data signal generated by beamformer 1202 on lead 1204 is supplied directly to scan converter 1210 instead of detector 1205. The output of scan converter 1210 is supplied to detector 1205 and data compression device 1208 and the output signal of amplifier 1208 is supplied to monitor 1212 for display.

Figure 12:
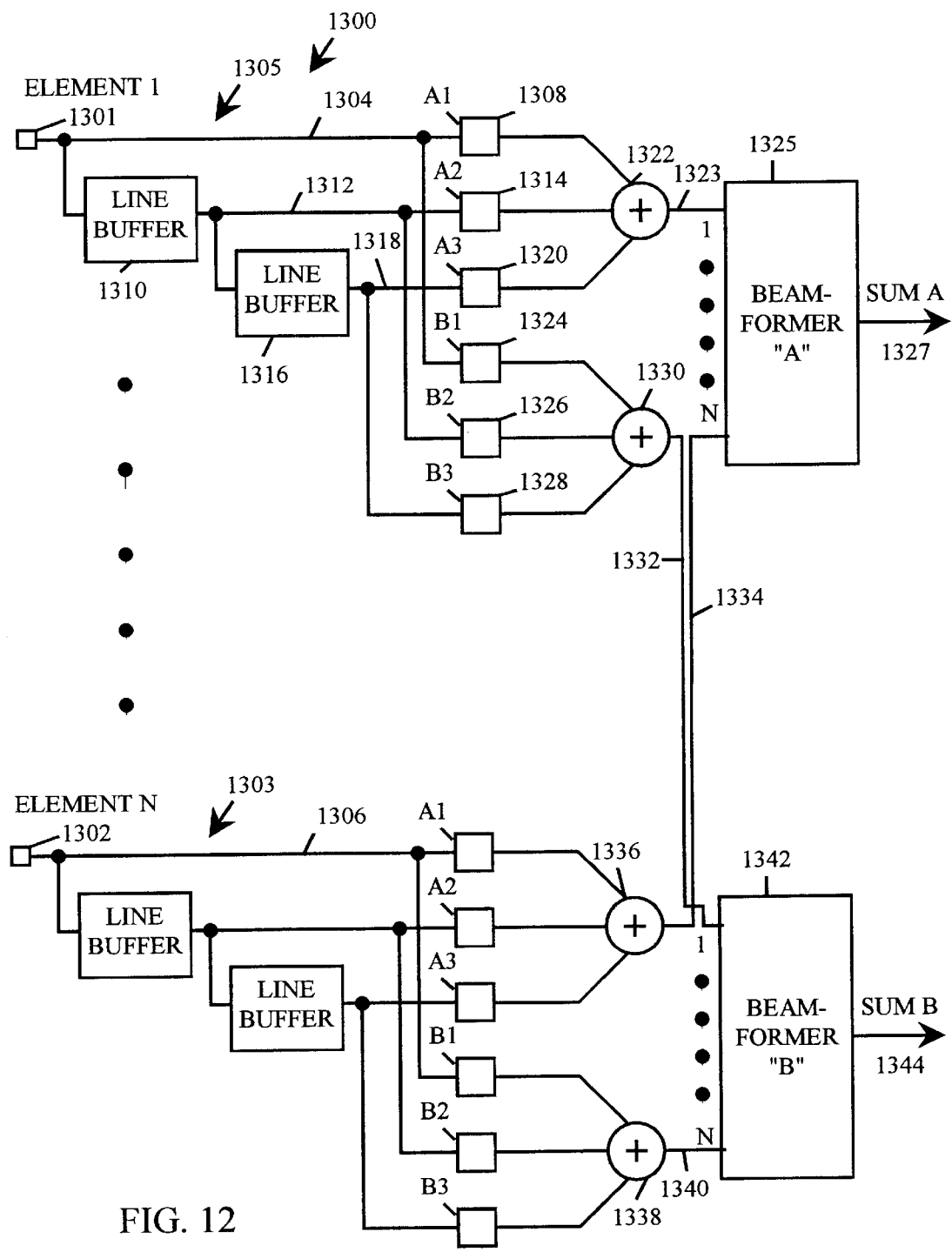
FIG. 12 is a schematic diagram showing an acoustic circuit in which acoustic elements are connected to a plurality of beamformers by interpolation circuits.

Referring to FIG. 12, a schematic diagram shows an acoustic circuit 1300 in which the acoustic elements are connected to a plurality of beamformers by interpolation circuits. The acoustic circuit 1300 is used to synthesize additional line information from existing transducer receive outputs signals. The acoustic circuit 1300 has transducer elements, including illustrated elements 1301 and 1302, that are connected to associated beamformers, including respective illustrated beamformers 1325 and 1342, through an interpolation circuit, including respective illustrated interpolation circuits 1305 and 1303 are shown. Illustratively the individual interpolation circuits are identical. The acoustic circuit 1300 shows generation of only two synthesized beams to reduce complexity. In general, the transducer output information is typically used to synthesize three or more receive lines.

An output signal from element 1301 on lead 1304 is supplied to a pair of line-generator circuits; a first circuit includes multipliers 1308, 1314, and 1320, and summing junction 1322, and a second line-generator circuit includes multiplier 1324, 1326, and 1328, and summing junction 1330. In the first line-generator circuit, output lead 1304 is connected directly to multiplier 1308 and to an input terminal of line buffer 1310. Line buffer 1310 delays the output 1304 for a time period equivalent to the transmit and receive time of the system so that the output signal 1312 of line buffer 1310 includes the output signal from transducer 1301 for the previous acoustic line.

Output signal 1312 is supplied to a second line buffer 1316, so that the output signal from the latter buffer on lead 1318 includes the output signal 1304 from transducer 1301 delayed by two line time periods. The output signals 1312 and 1318 of line buffers 1310 and 1316 are respectively supplied to multipliers 1314 and 1320.

Multipliers 1308, 1314, and 1320 are supplied with constants A1, A2 and A3, respectively, that scale the transducer and line buffer output signals. Each multiplier supplies a scaled output signal to a summing junction 1322. The scaling and summing synthesizes a new receive value on the output line 1323 of summing junction 1322 from the transducer output line 1304 from the receive information available for three consecutive transmit lines. The synthesized output signal is supplied to one input terminal of a convention beamformer 1325.

The output signal of transducer 1301 on line 1304 and the output signals 1312 and 1318 of line buffers 1310 and 1316 are also supplied to three additional multipliers 1324, 1326 and 1328. The multipliers 1324, 1326 and 1328 are supplied with three different scaling constants B1, B2 and B3, and the scaled output signals are applied to summing junction 1330 to generate an additional synthesized output signal. If the A and B constants differ, the second synthesized output signal differs from the first synthesized output signal. The latter synthesized output signal on line 1332 of summing junction 1330 is supplied to the first input terminal of a second conventional beamformer 1342.

Beamformer 1325 generates an output signal on lead 1327 and beamformer 1342 generates an output signal on lead 1344. The output signals can be stored and processed as if twice the actual number of lines were acquired.

A similar interpolation circuit is included for the output signals of the individual transducer elements. For example, interpolation circuit 1303 is connected at the output terminal of transducer element 1302. The individual interpolation circuits generate two synthesized lines. One line is connected to one input terminal of beamformer 1325 and the other line is connected to one input terminal of beamformer 1342. The output signals from interpolation circuit 1303 generated by summing junctions 1336 and 1338 are provided via lines 1334 and 1340 as the "n" input to beamformer 1325 and 1342, respectively.

One problem with the acoustic circuit 1300 is that two line-generating circuits are connected to each transducer output terminal resulting in a total of 2N line-generator circuits, increasing the cost of the circuit.

Figure 13:
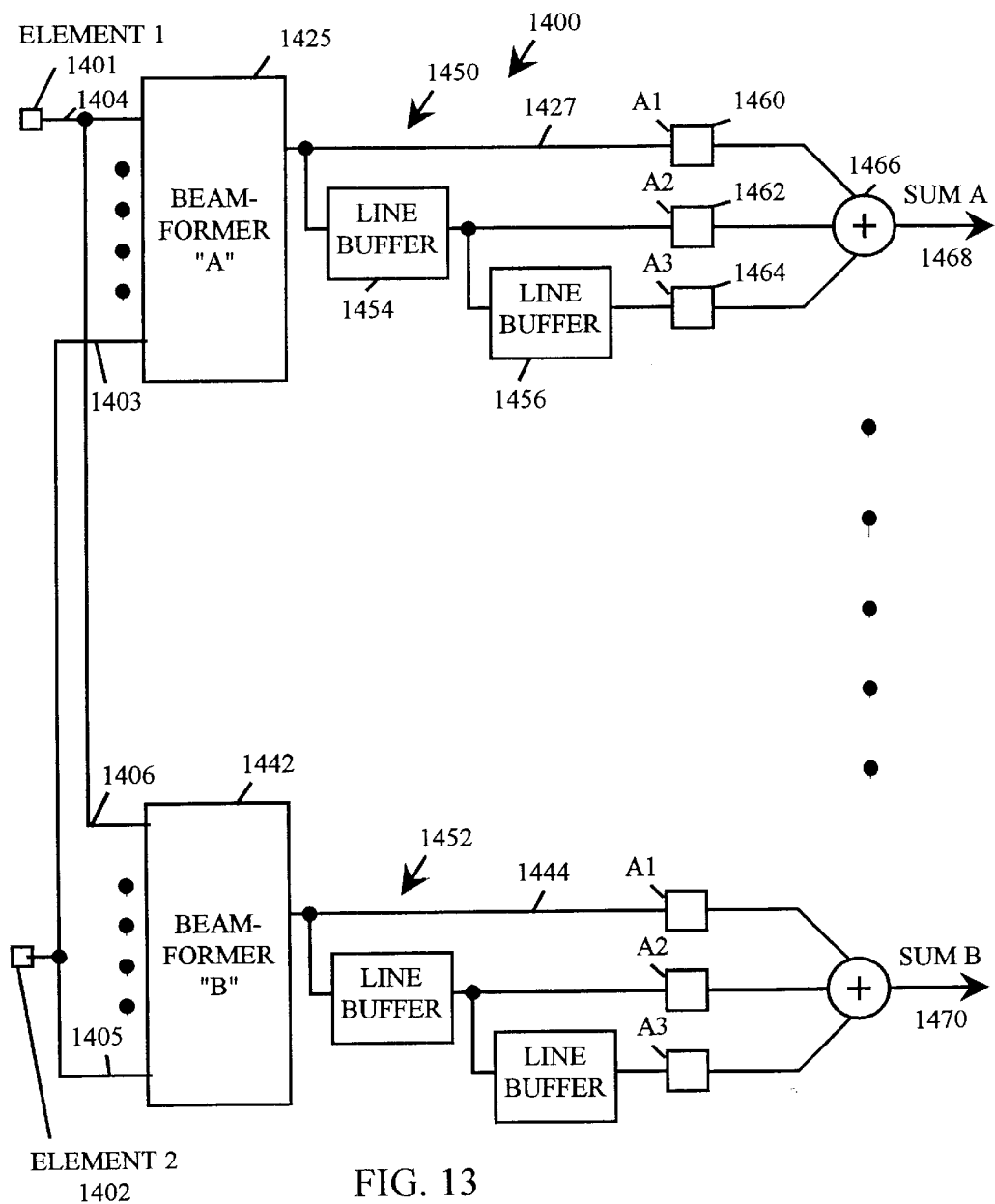
FIG. 13 is a modification of the circuitry shown in FIG. 12 in which a plurality of interpolation circuits is connected to the output terminals of a plurality of beamformers to reduce the number of acoustic scan lines necessary to reconstruct the image.

Referring to FIG. 13, a modified version of acoustic circuit 1300 is shown in which a plurality of interpolation circuits are connected to the output terminal of a plurality of beamformers to reduce the number of acoustic scan lines for reconstructing an image. The modified acoustic circuit 1400 performs interpolation after beamforming to reduce the number of line-generating circuits.

Specifically, output terminals of N receive transducer elements, of which elements 1401 and 1402 are shown, are connected to two beamformers 1425 and 1442. More particularly, the output signal from transducer element 1401 is connected via lead 1404 to beamformer 1425 and also connected via lead 1406, to beamformer 1442. Similarly, the output signal from transducer 1402 is connected via lead 1403, to beamformer 1425 and, via lead 1405, to beamformer 1442.

Output signals from the beamformers 1425 and 1442 are connected to an interpolation circuit. For example, the output signal from beamformer 1425 on lead 1427 is connected to interpolation circuit 1450. Similarly, output signal 1444 from beamformer 1442 is connected to interpolation circuit 1452. Interpolation circuits 1450 and 1452 are essentially equivalent.

Interpolation circuit 1450 includes two line buffers 1454 and 1456, three multipliers 1460-1464 and a summing junction 1466. Multiplier 1460 multiplies the output of beamformer 1425 by a predetermined constant Al and supplies the scaled output signal to summing junction 1466. The output signal from beamformer 1425 is also applied to line buffer 1454 which delays the output signal for a time period equal to an acoustic line time duration. The output signal from line buffer 1454 on lead 1458 is supplied to multiplier 1462 for multiplication by a second constant A2 and applied to summing junction 1466. The output signal from line buffer 1454 on lead 1458 is also supplied to line buffer 1456 for delay by the acoustic line time duration. The output signal from line buffer 1456 is applied to multiplier 1464 for multiplication by a constant A3. The scaled output signal is supplied to summing junction 1466.

By suitably adjusting the constants A1–A3, a sum is formed at the output terminal 1468 of summing junction 1466 which is the interpolated output signal of beamformer 1425 derived from three successive acoustic line scans.

Interpolator 1452 operates in a similar manner to generate a second interpolated output on lead 1470. The constants and the multipliers in interpolator 1452 are adjusted to the same values of the multipliers in interpolator 1450. The circuit operates in a similar manner to that shown in FIG. 12 except that only two interpolation circuits are employed rather than 2N interpolation circuits.

When two receive beams are synthesized for each transmit beam, a signal-to-noise ratio loss occurs because the synthesized transmit beams do not return along the path taken by the transmit beam. A "checkerboard" artifact may also be produced since all synthesized receive lines don't have identical beam profiles. To eliminate the signal-to-noise penalty and possible artifacts, three beamformers can be used to generate three output signals from the received data from each actual transmit beam. The beamformer output signals are generated at the sequence of angles given in the Table I for each transmit angle:

TABLE I

| Transmit Angle | Beamformer 1 Receive Angle | Beamformer 2 Receive Angle | Beamformer 3 Receive Angle |
|---|---|---|---|
| . | . | . | . |
| . | . | . | . |
| . | . | . | . |
| 0 | 0 | −ΔΘ/2 | ΔΘ/2 |
| ΔΘ | ΔΘ | ΔΘ/2 | 3ΔΘ/2 |
| 2ΔΘ | 2ΔΘ | 2ΔΘ/2 | 5ΔΘ/2 |
| 3ΔΘ | 3ΔΘ | 3ΔΘ/2 | 7ΔΘ/2 |
| . | . | . | . |
| . | . | . | . |

To synthesize round-trip receive line information, the output signals from the beamformers are stored in a memory and the stored output signals are combined to generate the synthesized receive beams. A suitable combination is shown in Table II:

TABLE II

| Synthesized Round-Trip Angle | Linear Combination for Synthesis of Round-Trip Beam |
|---|---|
| . | . |
| . | . |
| . | . |
| 0 | R1(0) |
| $\Delta\Theta/2$ | $0.68*[R2(\Delta\Theta) + R3(0)]$ |
| $\Delta\Theta$ | $R1(\Delta\Theta)$ |
| $3\Delta\Theta/2$ | $0.65*[R2(2\Delta\Theta) + R3(\Delta\Theta)]$ |
| $2\Delta\Theta$ | $R1(2\Delta\Theta)$ |
| . | . |
| . | . |
| . | . | where Rn(x) is the stored output signal generated by beamformer n from a transmit beam at steering angle x. Table II indicates that synthesized round-trip receive beam data is generated by averaging data from transmit beams at two different steering angles. Combining data from two transmit beams attains an image similar to an image generated with a third transmit beam interposed between the two.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. An ultrasound device for controlling a two-dimensional ultrasonic transducer array comprising:
    a signal transmitter, coupled to the two-dimensional ultrasonic transducer array, that forms, steers, and selectively focuses ultrasonic beams to insonify a volume; and
    a controller that controls the signal transmitter to deliver therapy to the volume.

2. An ultrasound device according to claim 1 further comprising:
    a signal receiver, coupled to the two-dimensional ultrasonic transducer array, including devices that detect echoes from the three-dimensional volume field; and
    the controller controlling the signal transmitter and signal receiver to simultaneously form images and deliver a therapy to the three-dimensional field.

3. An ultrasound device according to claim 2 wherein:
    the controller is capable of controlling beam forming and focusing to scan a focal point of the ultrasonic beam in a pattern within an identified volume structure of a image.

4. An ultrasound device according to claim 2 wherein:
    the controller is capable of controlling beam forming and focusing to scan a field of view in a sharply focused beam that is suitable in resolution and intensity for simultaneous diagnostic imaging and delivery of therapy, the sharply focused beam being scanned throughout the imaged volume to have a uniform insonation.

5. An ultrasound device according to claim 2 wherein:
    the controller is capable of controlling beam forming and focusing to defocus the beam to match the cross-sectional size of the tissue-of-interest and direct the resulting broad beam to the tissue-of-interest, the broad beam being defocused to have a uniform insonation.

6. An ultrasound device according to claim 2 wherein:
    the controller is capable of controlling beam forming and focusing to deliver a therapy including a hyperthermia therapy or a therapy utilizing delivery of a pharmaceutical via microspheres.

7. An ultrasound device according to claim 2 wherein:
    the controller is capable of controlling beam forming and focusing to deliver pulsed ultrasound signals at intensity levels that heat tissue and burst microspheres when pulsed, the reflected pulses being detected and processed to form a diagnostic image.

8. An ultrasound device according to claim 2 wherein:
    the controller is capable of controlling beam forming and focusing in two or three dimensions through an interrogation volume in the form of a plurality of geometries including a spherical geometry and an ellipsoidal geometry.

9. An ultrasound device according to claim 1 further comprising:
    the two-dimensional ultrasonic transducer array.

10. An ultrasound device according to claim 1 further comprising:
    an ultrasound signal acquisition circuit;
    an ultrasound image display circuit, and
    a processor.

11. A method of delivering an ultrasound therapy to a biological tissue comprising:
    insonating the biological tissue in an ultrasonic scan of a selected field of view using a two-dimensional ultrasonic transducer array and a transmitter including devices that form, steer, and selectively focus ultrasonic beams in a three-dimensional volume field; and
    delivering a therapy to the tissue-of-interest within the three-dimensional volume field with uniform insonation.

12. A method according to claim 11 further comprising:
    insonating the biological tissue in the ultrasonic scan of the selected field of view using the two-dimensional ultrasonic transducer array and a receiver that detects echoes from the three-dimensional volume field;
    imaging the biological tissue from the detected echoes; and
    localizing a tissue-of-interest within the selected field of view.

13. A method according to claim 11 further comprising:
    controlling delivery of a therapeutic substance to the tissue-of-interest including:
        administering microspheres containing a pharmaceutical substance to a patient;
        monitoring the microspheres during the imaging operation to determine whether the microspheres are present within the tissue-of-interest; and
        rupturing the microspheres using ultrasound to release the therapeutic substance into the tissue-of-interest.

14. A method according to claim 11 further comprising:
controlling delivery of the therapy to the tissue-of-interest, the therapy being selected from among a hyperthermia therapy, a hyperthermia therapy using microspheres to enhance heating, a local delivery of a bioactive composition via microspheres, a hyperthermia therapy that enhances uptake of pharmaceuticals in the bloodstream, a hyperthermia therapy that enhances the transport rate of a thrombolytic substance.

15. A method according to claim 11 further comprising:
scanning an ultrasonic beam focal point in a pattern within the identified tissue-of-interest to attain uniform insonation within the tissue-of-interest.

16. A method according to claim 11 further comprising:
controlling beam forming and focusing to scan a field of view in a sharply focused beam that is suitable in resolution and intensity for simultaneous diagnostic imaging and delivery of therapy, the sharply focused beam being focused throughout the imaged volume to have a uniform insonation.

17. A method according to claim 11 further comprising:
controlling beam forming and focusing to defocus the beam to match the cross-sectional size of the tissue-of-interest and direct the resulting broad beam to the tissue-of-interest, the broad beam being defocused to have a uniform insonation.

18. A method according to claim 11 further comprising:
controlling beam forming and focusing to defocus the beam to match the cross-sectional size of the tissue-of-interest and direct the resulting broad beam to the tissue-of-interest, the broad beam being defocused to have a uniform insonation.

19. A method according to claim 11 further comprising:
controlling beam forming and focusing to deliver a therapy including a hyperthermia therapy or a therapy utilizing delivery of a pharmaceutical via microspheres.

20. A method according to claim 11 further comprising:
controlling beam forming and focusing to deliver pulsed ultrasound signals at intensity levels that heat tissue and burst microspheres when pulsed, the reflected pulses being detected and processed to form a diagnostic image.

21. A method according to claim 11 further comprising:
controlling beam forming and focusing to generate an interrogation volume in the form of a plurality of geometries including a spherical geometry and an ellipsoidal geometry.

22. An ultrasound device comprising:
means for insonating the biological tissue in an ultrasonic scan of a selected field of view using a two-dimensional ultrasonic transducer array and a transmitter including devices that form, steer, and selectively focus ultrasonic beams in a three-dimensional volume field; and
means for delivering a therapy to the tissue-of-interest within the three-dimensional volume field with uniform insonation.

23. An ultrasound device according to claim 22 further comprising:
means for insonating the biological tissue in the ultrasonic scan of the selected field of view using the two-dimensional ultrasonic transducer array and a receiver that detects echoes in the three-dimensional volume field;
means for imaging the biological tissue from the detected echoes; and
means for localizing a tissue-of-interest within the selected field of view.

24. An ultrasound device according to claim 22 further comprising:
means for controlling delivery of a therapeutic substance to the tissue-of-interest including:
means for administering microspheres containing a pharmaceutical substance to a patient;
means for monitoring the microspheres during the imaging operation to determine whether the microspheres are present within the tissue-of-interest; and
means for rupturing the microspheres using ultrasound to release the therapeutic substance into the tissue-of-interest.

* * * * *